(12) United States Patent
Leedy (10) Patent No.: US 9,980,781 B2
(45) Date of Patent: May 29, 2018

(54) BREAST IMPLANT SIZER ASSEMBLY AND METHOD

(71) Applicant: Jason Leedy, Mayfield Heights, OH (US)

(72) Inventor: Jason Leedy, Mayfield Heights, OH (US)

( * ) Notice: Subject to any disclaimer, the term of this patent is extended or adjusted under 35 U.S.C. 154(b) by 0 days. days.

(21) Appl. No.: 15/215,613

(22) Filed: Jul. 21, 2016

(65) Prior Publication Data

US 2017/0020620 A1    Jan. 26, 2017

Related U.S. Application Data

(60) Provisional application No. 62/194,851, filed on Jul. 21, 2015.

(51) Int. Cl.
*A61F 2/12*     (2006.01)
*A61B 90/00*    (2016.01)

(52) U.S. Cl.
CPC ............... *A61B 90/06* (2016.02); *A61F 2/12* (2013.01); *A61B 2090/063* (2016.02); *A61F 2240/005* (2013.01); *A61F 2250/0003* (2013.01); *A61F 2250/0004* (2013.01)

(58) Field of Classification Search
CPC ........................................................ A61F 2/12
USPC ........................................................ 623/7–8
See application file for complete search history.

(56) References Cited

U.S. PATENT DOCUMENTS

| | | | |
|---|---|---|---|
| 6,796,875 B1 | 9/2004 | Placik | |
| 6,936,068 B1 * | 8/2005 | Knisley | A61F 2/52 623/7 |
| 6,981,988 B1 | 1/2006 | Kinsley | |
| 8,784,486 B2 | 7/2014 | Schuessler | |
| 2007/0233273 A1 * | 10/2007 | Connell | A61F 2/12 623/23.72 |
| 2009/0099588 A1 * | 4/2009 | Makower | A61F 5/0073 606/191 |
| 2009/0149953 A1 | 6/2009 | Schuessler et al. | |
| 2009/0326654 A1 * | 12/2009 | Powell | A61F 2/12 623/8 |
| 2011/0046729 A1 * | 2/2011 | Schuessler | A61F 2/12 623/8 |

(Continued)

OTHER PUBLICATIONS

PCT International Search Report and Written Opinion for PCT/US2016/043227, dated Nov. 2, 2016, pp. 1-13.

*Primary Examiner* — Suzette J Gherbi
(74) *Attorney, Agent, or Firm* — Tarolli, Sundheim, Covell & Tummino LLP (57) ABSTRACT

One aspect of the present disclosure relates to a breast implant sizer assembly for accurately sizing surgically implantable breast implants prior to implantation. The breast implant sizer assembly can include an inflatable, flexible shell containing an adjustable volume of liquid and a valve assembly, once filled with liquid, that is associated with the shell and configured like an anatomically correct nipple. The breast implant sizer assembly can have a size, shape, and weight that mimics the size, shape, and weight of a breast implant. In addition, the breast implant sizer assembly is disposable, intended for single use by a patient, allows for use in the home and everyday settings, and provides accurate, actionable information to a surgeon or other medical professional in regards to selecting actual breast implant sizes for clinical use.

12 Claims, 5 Drawing Sheets

(56) References Cited

U.S. PATENT DOCUMENTS

| | | | | |
|---|---|---|---|---|
| 2013/0013063 A1* | 1/2013 | Del Vecchio | ............. | A61F 2/12 623/8 |
| 2013/0317610 A1* | 11/2013 | Ledergerber | ............. | A61F 2/12 623/8 |
| 2014/0100656 A1* | 4/2014 | Namnoum | ............. | A61L 27/20 623/8 |
| 2014/0336759 A1* | 11/2014 | Martin | ............. | A61F 2/12 623/8 |
| 2015/0272723 A1* | 10/2015 | Hristov | ............. | A61F 2/12 623/8 |
| 2017/0065403 A1* | 3/2017 | Al-Jasim | ............. | B29C 41/14 |

\* cited by examiner

Fig. 5B ously filled with liquid, can have a size, shape, and weight that mimics the size, shape, and weight of a breast implant.

BREAST IMPLANT SIZER ASSEMBLY AND METHOD

RELATED APPLICATION

This application claims the benefit of U.S. Provisional Patent Application Ser. No. 62/194,851, filed Jul. 21, 2015, the entirety of which is hereby incorporated by reference for all purposes.

TECHNICAL FIELD

The present disclosure relates generally to apparatus and methods for accurately sizing surgically implantable breast implants prior to implantation.

BACKGROUND

Surgical implantation of material in human female breasts has become fairly common, both for medical reconstructive and for cosmetic purposes. A key factor in such surgery is the proper selection of the size of the prosthetic implant. Currently, patients and physicians typically make their choices based on anatomic factors or using crude and unwieldy devices, such as tape measures, balloons filled with water, or home-based options (e.g., filling bags with rice).

SUMMARY

In one aspect of the present disclosure, a breast implant sizer assembly can comprise an inflatable, flexible shell containing an adjustable volume of liquid and a valve assembly that is associated with the shell and configured like an anatomically correct nipple. The breast implant sizer assembly, once filled with liquid, can have a size, shape, and weight that mimics the size, shape, and weight of a breast implant.

Another aspect of the present disclosure can include a method for selecting a properly sized breast implant. One step of the method can include determining, by a candidate for surgical implantation of a breast implant, a preferred breast implant based on use of one or more breast implant sizer assemblies. Each breast implant sizer assembly can comprise an inflatable, flexible shell containing an adjustable volume of liquid and a valve assembly that is associated with the shell and configured like an anatomically correct nipple. The breast implant sizer assembly, once filled with liquid, can have a size, shape, and weight that mimics the size, shape, and weight of a breast implant. The candidate can consult with a medical professional to determine if the preferred breast implant is appropriate for implantation.

Another aspect of the present disclosure relates to a breast implant sizer assembly consisting of an inflatable, flexible shell, a valve assembly, and a cap. The shell can contain an adjustable volume of liquid. The valve assembly can be directly connected to, and integral with, the shell. The cap can be mated with the valve assembly. The cap can be configured to occlude the port so that a liquid does not leak from the shell during use of the breast implant sizer assembly. The combination of the cap and the valve assembly can provide the breast implant sizer assembly with the appearance of an anatomically correct nipple. The breast implant sizer assembly, once filled with liquid, can have a size, shape, and weight that mimics the size, shape, and weight of a breast implant.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 1B is a perspective view showing the breast implant sizer assembly of

FIG. 1A in an exploded configuration;

DETAILED DESCRIPTION

I. Definitions

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the terms "candidate", "subject", and "patient" can be used interchangeably and refer to a human being.

II. Overview

The present disclosure relates generally to apparatus and methods for accurately sizing surgically implantable breast implants prior to implantation. Conventional apparatus and methods for sizing breast implants prior to implantation suffer from several drawbacks. Current available options include using balloons filled with water, manufacturer-provided actual breast implants or intraoperative breast implant sizers, 3D imaging equipment allowing virtual surgery, or the classic rice-in-pantyhose sizers. The newer options include sizing gel pads to be worn with clothing in the physician's office. One drawback to these techniques is that they must be done in a physician's office, which causes the candidate to make decisions in a stressful, rushed environment that can lead to regretful decisions. The exception is the balloon and water or the rice and pantyhose options, which are available for candidates to try at home. However, these crude methods do not approximate actual breast implant dimensions and therefore are inaccurate.

Manufacturer-provided actual breast implants, actual intraoperative breast implant sizers, or the newer sizing gel pads are currently the best methods for determining desired breast implant size. Actual breast implants, intraoperative breast implant sizers (which are intended to be temporarily placed within the breast at the time of surgery), and sizing gel pads are costly, however, and therefore are not designed for disposable consumption by the end user and are only available in the physician's office requiring decisions by candidates under stressful conditions. Additionally, gel pad sizers do not accurately simulate the weight associated with breast implants. Further, since actual breast implants, intraoperative breast implant sizers, and sizing gel pads are used by multiple patients and placed on bare skin and nipple and areolas, they do require proper cleaning in between each use which limits their practicality. Alternative and less desirable options to determine breast implant sizes involve fluid-filled or solid reservoirs that are to be placed within a specialized bra. These techniques are akin to trying padded bras and do not accurately represent size, shape, and weight of actual breast implants and therefore have limited utility for both the candidate and surgeon in making clinical decisions.

Advantageously, the present disclosure provides breast implant sizer assemblies 10 (FIGS. 1A-B) and related methods that better educate potential breast implant candidates about breast implant sizes while also providing actionable information for a surgeon or medical professional in making clinical decisions, which together improve the consumer experience. The breast implant sizer assemblies 10 of the present disclosure are not intended to determine proper implant size per se; rather, it is the combination of the breast implant sizer assemblies along with proper feedback and assessment from a medical professional (e.g., a physician or surgeon) that improves the consumer experience and educates candidates about their choices. Further, the breast implant sizer assemblies 10 of the present disclosure, once filled with liquid, mimic the size, weight, and shape of breast implants. This advantageously allows candidates to gain a realistic understanding of life with breast implants prior to implantation surgery and thus better educate candidates on their decision.

By allowing the candidate to use the sizers in the comfort of their own home, they can make their decisions in a stress-free environment and can use the sizers in a variety of everyday scenarios (e.g., grocery shopping, exercise, etc.). In addition, by being economical, these sizers are disposable and intended for single use, which avoids necessary cleaning between uses as required for current techniques. As discussed in more detail below, the present disclosure provides breast implant sizer assemblies 10 that, once filled with liquid, mimics the size, weight, and shape of actual breast implants while allowing for end use by the consumer in the comfort of their own home with the added benefit of providing actionable information to a surgeon (or other medical professional), which in total will improve the consumer experience in reaching breast implant sizing decisions.

III. Breast Implant Sizer Assemblies

One aspect of the present disclosure can include a breast implant sizer assembly 10 for accurately sizing surgically implantable breast implants prior to implantation. As discussed in more detail below, a breast implant sizer assembly 10 can comprise a number of integrated components, including a shell 12, a valve assembly 14, a shell disc 16, a fabric pad 18, and an inserter 20. Advantageously, the breast implant sizer assembly 10, once filled with liquid, has a size, shape, and weight that mimics the size, shape, and weight of a breast implant, which helps candidates determine the proper size and better understand what to expect after surgical implantation of a breast implant.

Figure 1A:
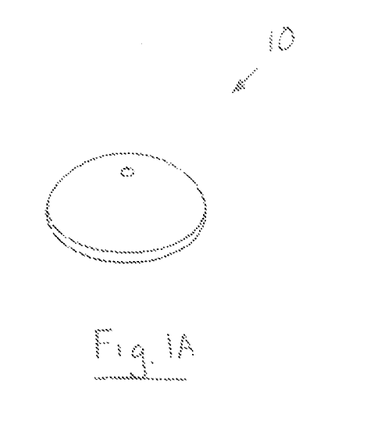
FIG. 1A is perspective view showing a breast implant sizer assembly, in an assembled configuration, constructed in accordance with one aspect of the present disclosure.
Figure 1B:
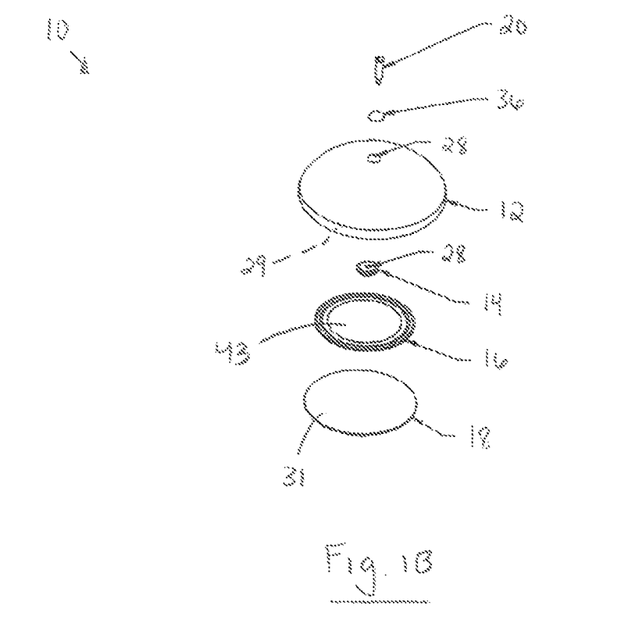

As shown in FIG. 1A, one component of the breast implant sizer assembly 10 can include an inflatable, flexible, and resilient shell 12 that is formed of a suitable elastic and fluid-impermeable material (e.g., neoprene, vinyl, latex and the like). The shell 12 is capable of holding an adjustable volume of liquid, such as water or saline. In other words, the shell 12 can be sized and dimensioned to accommodate (hold) various pre-determined liquid volumes (e.g., by virtue of the elastic material used to form the shell) while still maintaining the size, shape, and weight of an actual breast implant. The shell 12 can hold any desired volume of liquid within a recommended fill range based on the dimensions of the shell. For example, the shell 12 can hold less than about 250 cc of a liquid, about 250 cc of a liquid, about 300 cc of a liquid, about 350 cc of a liquid, about 400 cc of a liquid, or about 450 cc or more of a liquid. A given shell 12 can have a particular set of dimensions or a configuration so that the shell, once filled, will accurately reflect the dimensions of actual breast implants.

An anterior portion 22 of the shell 12 can include a surface 24 having a slight curvature that generally corresponds to the curvature seen with actual breast implants used for surgery at a desired liquid volume. A posterior portion 26 of the shell 12 has a flattened (or substantially flattened)

configuration that allows the shell to rest against the skin (e.g., the breast) of a breast implant candidate. The shell 12 is completely closed except for a port 28, which is located at the anterior portion 22 of the shell and extends through the surface 24 thereof. The port 28 can provide access to a source of liquid for introducing the liquid into the shell 12 to inflate it or, alternatively, for removing fluid from the shell to deflate it. Inflation and deflation of the shell 12 can be effected by a suitable apparatus, such as a syringe.

Figure 2A:
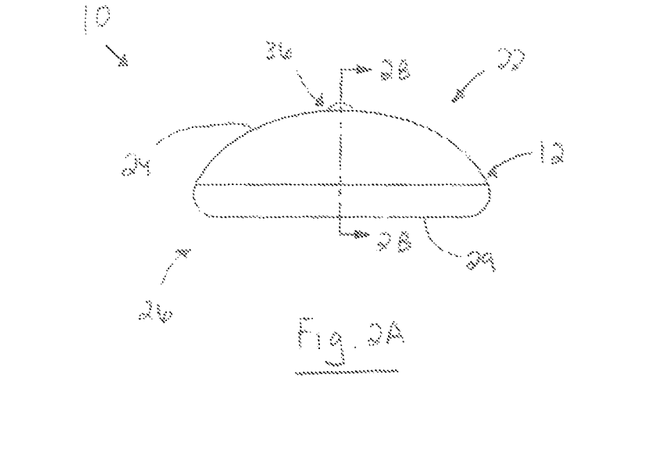
FIG. 2A is a schematic illustration showing a side view of the breast implant sizer assembly in FIG. 1A.
Figure 2B:
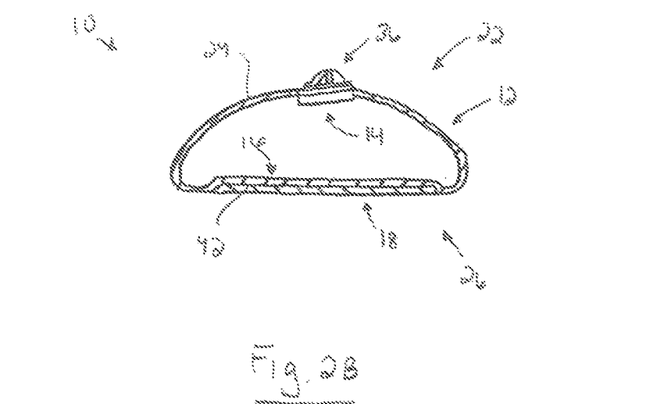
FIG. 2B is a cross-sectional view taken along Line 2B-2B in FIG. 2A.
Figure 3:
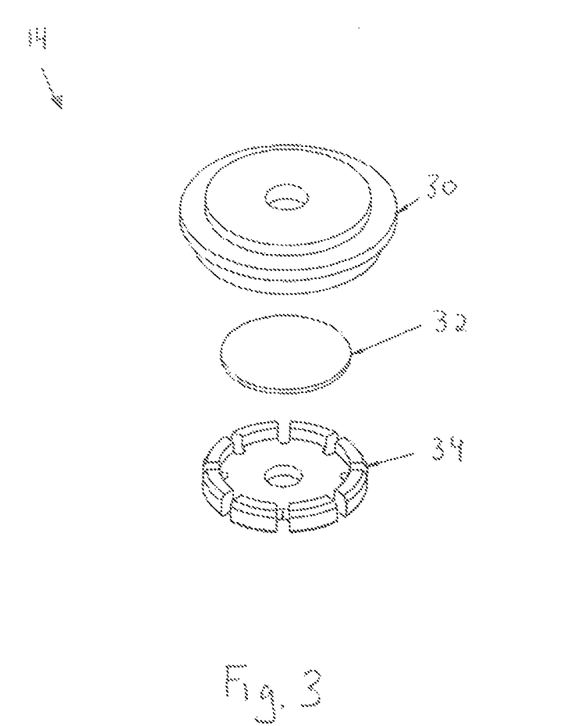
FIG. 3 is a perspective view showing a valve assembly, in an exploded configuration, comprising the breast implant sizer assembly in FIGS. 1A-B.
Figure 5A:
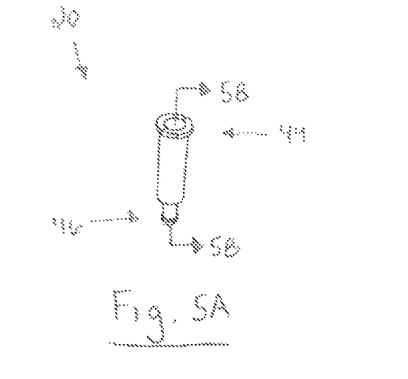
FIG. 5A is a perspective view of an inserter for mating with the valve assembly in FIG. 3.
Figure 5B:
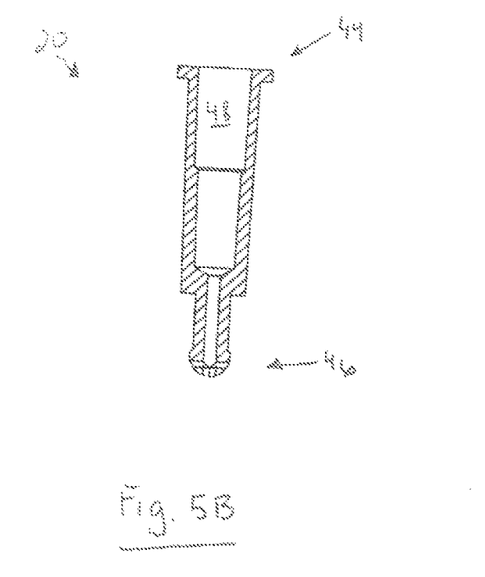
FIG. 5B is a cross-sectional view taken along Line 5B-5B in FIG. 5A.

As shown in FIGS. 2A-B, the valve assembly 14 is connected (e.g., directly connected) to, and integral with, the shell 12 (e.g., by friction fit, adhesive, extrusion process, etc., as would be appreciated by one skilled in the art). The valve assembly 14 (FIG. 3) can comprise a valve seat 30, a seal 32 (or diaphragm), and a valve back 34. When assembled, the seal 32 rests between the valve seat 30 and the valve back 34. Advantageously, when compression is applied to the liquid within the shell 12, the liquid pushes the seal 32 up against the port 28 of the valve seat 30, thereby sealing the port and preventing loss of the liquid from the shell. In some instances, the valve assembly 14 can be penetrated by an inserter 20 (FIGS. 5A-B) or a filling needle (not shown) such that liquid may be injected into the shell 12, but liquid cannot escape through the valve assembly once the inserter or filling needle is withdrawn.

Figure 4A:
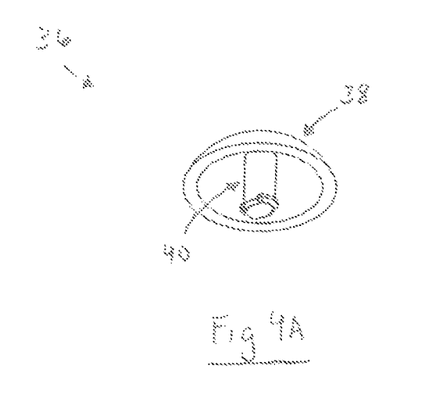
FIGS. 4A-B are schematic illustrations of a cap comprising the breast implant sizer assembly in FIGS. 1A-B.
Figure 4B:
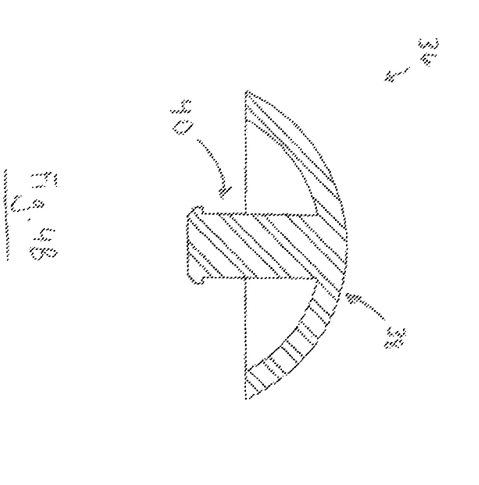

The breast implant sizer assembly 10 also includes a cap 36 (FIGS. 4A-B) that is sized and dimensioned to mate with the valve assembly 14. The cap 36 can be configured to occlude the port 28 so that liquid does not leak from the shell 12 when the breast implant sizer assembly 10 is being used. As shown in FIGS. 4A-B, the cap 36 can comprise an upper dome-shaped portion 38 and a post member 40 that is connected (e.g., directly connected), and extends transverse to, the upper dome-shaped portion (e.g., using an adhesive or integrally, e.g., as part of a polymer manufacturing/extrusion process, as would be appreciated by one skilled in the art). The combination of the cap 36 with the valve assembly 14 provides the breast implant sizer assembly 10 with the appearance of an anatomically correct nipple. This configuration advantageously allows candidates to correctly orient the breast implant sizer assembly 10 and therefore accurately mimic the results obtainable with a breast implant.

Referring again to FIG. 1B, the breast implant sizer assembly 10 further includes a shell disc 16 and a fabric pad 18. The shell disc 16 can be a relatively thin and rigid (or semi-rigid) piece of material configured to provide structural support for the shell 12, while also allowing the posterior portion 26 of the shell to conform to the skin (e.g., breast tissue) of the subject. The shell disc 16 has a lower surface 42 that is adapted to receive the fabric pad 18 (e.g., so that an upper surface 31 of the fabric pad is connected, e.g., directly connected, to the lower surface 42) (e.g., using an adhesive or other fastener known to those skilled in the art). The shell disc 16 has an upper surface 43 that is connected (e.g., directly connected) to a lower surface 29 of the shell 12 (e.g., using an adhesive or other fastener known to those skilled in the art). The fabric pad 18 can be made of felt, for example, and advantageously improves comfort of the breast implant sizer assembly 10 during use.

As mentioned above, an inserter 20 (FIGS. 5A-B) can be used to introduce a liquid into the shell 12. The inserter 20 can have a generally conical shape comprising a first end 44 and a second end 46. The second end 46 is adapted for insertion into the port 28 of the valve assembly 14. The inserter 20 can also include a channel 48 that extends between the first and second ends 44 and 46. The portion of the channel 48 at the first end 44 of the inserter 20 can be configured to receive a liquid source, such as a syringe.

IV. Method

Another aspect of the present disclosure can include a method for selecting a properly sized breast implant. The method can generally include the steps of: determining, by a candidate for surgical implantation of a breast implant, a preferred breast implant based on use of one or more breast implant sizer assemblies 10, each breast implant sizer comprising an inflatable, flexible shell 12 containing an adjustable volume of liquid and a valve assembly 14 that is associated with the shell and configured like an anatomically correct nipple, the shell (once filled) having a size, shape, and weight that mimics the size, shape, and weight of a breast implant; and consulting, by the candidate, with a medical professional to determine if the preferred breast implant is appropriate for implantation in the candidate.

In some instances, a candidate for surgical implantation of a breast implant can determine a preferred breast implant prior to consulting with a medical professional. In such instances, the candidate can order any number of breast implant sizer assemblies 10, each of which has a desired, adjustable volume of a liquid (e.g., water). The candidate can consult a sizer chart that provides desired end cup sizes based on different body and breast dimensions. The candidate can then wear each of the different breast implant sizer assemblies 10 to determine the preferred breast implant. After determining the preferred end cup size (and thus breast implant), the candidate can consult with a medical professional to determine if the preferred breast implant is appropriate for surgical implantation. The determination by the medical professional can be done, for example, by conducting a physical exam of the candidate. Based on information from the exam, the experience of the medical professional, and information about the breast implant sizer assembly 10 (and thus the preferred breast implant), the medical professional can recommend a proper sized breast implant.

In another aspect, the method can begin by having the candidate first consult with a medical professional, going through the sizing process with the medical professional, and then providing the candidate with one or more breast implant sizer assemblies 10 in the size range that the candidate is considering (and that is/are recommended by the medical professional). In such instances, the breast implant sizer assemblies 10 can be filled with a liquid by the medical professional, or their designee, as discussed above. Where a breast implant sizer assembly 10 is filled by the medical professional (or their designee), the process can begin by filling a syringe with a given amount of liquid (e.g., measured by graduation marks) and connecting the syringe to the valve assembly 14. The measured volume of liquid can then be injected into the shell 12. If necessary, liquid can be removed from the shell 12 to arrive at the desired volume of liquid in the shell.

Once the breast implant sizer assembly 10 is filled with the appropriate amount of liquid, the user will position the breast implant sizer assembly between one of her breasts and an article of clothing. For example, each breast implant sizer assembly 10 may be inserted over the breast between the breast and a bra. The candidate can then go about her usual activities while wearing the breast implant sizer assembly 10. During this time, the candidate can determine if the selected breast implant sizer assembly 10 is ideal and make adjustments to the volume as desired. After selecting the preferred breast implant sizer assembly 10, the candidate can again consult with the medical professional to confirm that a breast implant that mimics the selected breast implant sizer assembly is appropriate for implantation.

From the above description, those skilled in the art will perceive improvements, changes and modifications. Such improvements, changes and modifications are within the skill of one in the art and are intended to be covered by the appended claims.

What is claimed is:

1. A breast implant sizer assembly comprising:
an inflatable, flexible shell containing an adjustable volume of liquid;
a valve assembly that is associated with the shell and configured like an anatomically correct nipple; and
a cap that is sized and dimensioned to mate with the valve assembly, whereby the cap is configured to occlude a port of the shell so that a liquid does not leak from the shell during use of the breast implant sizer assembly;
wherein the breast implant sizer assembly, once filled with liquid, has a size, shape, and weight that mimics the size, shape, and weight of a breast implant.

2. The breast implant sizer assembly of claim 1, wherein the assembly is disposable and intended for single-use by a patient.

3. The breast implant sizer assembly of claim 1, wherein an anterior portion of the shell has a surface with a curvature that corresponds to the curvature of a breast implant.

4. The breast implant sizer assembly of claim 3, wherein a posterior portion of the shell has a flattened configuration that allows the shell to rest against the skin of a breast implant candidate.

5. The breast implant sizer assembly of claim 4, wherein the shell is completely closed except for the port, which is located at the anterior portion of the shell and extends through a surface of the shell.

6. The breast implant sizer assembly of claim 5, wherein the valve assembly further includes:
a valve seat;
a seal connected to the valve seat; and
a valve back connected to the seal;
wherein the seal rests between the valve seat and the valve back.

7. The breast implant sizer assembly of claim 6, wherein upon compression is applied to a liquid within the shell, the liquid pushes the seal up against the port to seal the port and prevent loss of the liquid from the shell.

8. The breast implant sizer assembly of claim 1, wherein the cap includes an upper dome-shaped portion and a post member that is connected, and extends transverse to, the upper dome-shaped portion.

9. The breast implant sizer assembly of claim 1, wherein the combination of the cap and the valve assembly provides the breast implant sizer assembly with the appearance of an anatomically correct nipple.

10. The breast implant sizer assembly of claim 1, further comprising:
a shell disc that is connected to a lower surface of the shell; and
a fabric pad that is connected to a lower surface of the shell disc.

11. A breast implant sizer assembly consisting of:
an inflatable, flexible shell containing an adjustable volume of liquid;
a valve assembly that is directly connected to, and integral with, the shell; and
a valve assembly that is directly connected to, and integral with, the shell; and
wherein the combination of the cap and the valve assembly provides the breast implant sizer assembly with the appearance of an anatomically correct nipple;
wherein the breast implant sizer assembly, once filled with liquid, has a size, shape, and weight that mimics the size, shape, and weight of a breast implant.

12. A breast implant sizer assembly comprising:
an inflatable, flexible shell containing an adjustable volume of liquid;
a shell disc that is connected to a lower surface of the shell;
a fabric pad that is connected to a lower surface of the shell disc; and
a valve assembly that is associated with the shell and configured like an anatomically correct nipple;
wherein the breast implant sizer assembly, once filled with liquid, has a size, shape, and weight that mimics the size, shape, and weight of a breast implant.

* * * * *